US009731043B2

(12) United States Patent
Lerouge et al.

(10) Patent No.: US 9,731,043 B2
(45) Date of Patent: Aug. 15, 2017

(54) EMBOLIZING SCLEROSING HYDROGEL

(71) Applicants: Val-Chum Limited Partnership, Montreal (CA); Socovar S.E.C., Montreal (CA)

(72) Inventors: Sophie Lerouge, Montreal (CA); Giles Soulez, Montreal (CA); Ahmed Fatimi, Montreal (CA); Jean-Michel Coutu, Montreal (CA); Jean Raymond, Montreal (CA)

(73) Assignees: VAL-CHUM, LIMITED PARTNERSHIP, Montreal, Quebec (CA); SOCOVAR S.E.C., Montreal, Quebec (CA)

( * ) Notice: Subject to any disclaimer, the term of this patent is extended or adjusted under 35 U.S.C. 154(b) by 407 days.

(21) Appl. No.: 14/483,274

(22) Filed: Sep. 11, 2014

(65) Prior Publication Data

US 2014/0377187 A1 Dec. 25, 2014

Related U.S. Application Data

(62) Division of application No. 13/112,289, filed on May 20, 2011, now Pat. No. 8,840,867.

(60) Provisional application No. 61/344,089, filed on May 20, 2010.

(51) Int. Cl.
*A61K 49/00* (2006.01)
*A01N 43/04* (2006.01)
*A61L 24/08* (2006.01)
*A61K 31/167* (2006.01)
*A61K 31/722* (2006.01)
*A61K 45/06* (2006.01)
*A61K 49/04* (2006.01)
*A61L 24/00* (2006.01)

(52) U.S. Cl.
CPC .......... *A61L 24/08* (2013.01); *A61K 31/167* (2013.01); *A61K 31/722* (2013.01); *A61K 45/06* (2013.01); *A61K 49/0457* (2013.01); *A61L 24/001* (2013.01); *A61L 24/0031* (2013.01); *A61L 2400/04* (2013.01); *A61L 2400/06* (2013.01); *A61L 2430/36* (2013.01)

(58) Field of Classification Search
CPC ... A61B 17/12181; A61B 6/481; A61B 8/481; A61K 49/0002
See application file for complete search history.

(56) References Cited

U.S. PATENT DOCUMENTS 6,344,488 B1 * 2/2002 Chenite ............ A61K 9/0019 424/422
2005/0008610 A1 1/2005 Schwarz et al.

OTHER PUBLICATIONS

Chabrol et al (Embolization and endothelial ablation with chitosan and sotradecol sulfate: Preliminary results in an animal model, Journal of Vascular and Interventional Radiology, vol. 21, Issue 2, S38039).*
Ganji et al (Gelation time and degradation rate of chitosan-based injectable hydrogel, Journal Sol-Gel Science Techn, vol. 42: pp. 47-53).*
Chabot et al. Abstract No. 97: Embolization and endothelial ablation with chitosan and sotradecol sulfate; Preliminary results in an animal model, Journal of Vascular and Interventional Radiology, 2010, vol. 21, pp. S38-S39.
Jean Raymond et al. (2002) Cyanoacrylate Embolization of Experimental Aneurysme. AM J. Neuroradiol 23, 129-138 Montreal,Canada Jan. 2002.
S. William Stavropoulos et al. 2005 Embolization of Type 2 Endoleaks After Endovascular Repair J. Vasc. Interv. Radiol 16, 857-861 Pennsylvania Nov. 2004.
S. William Stavropoulos et al. (2009) Type 2 Endoleak Embolization Comparison. Science Direct Journal of Vascular. vol. 20, Issue 10, 1299-1302 Pennslyvania Apr. 2000.
T.S. Maldonado et al. 2003 Initial Successful Management of Type 1 Endoleak After Endovascular. Journal of Vasucular Surgery vol. 38 No. 4665-670 New York Oct. 2003.
Michael L. Martin et al. (2001) Treatment of Type II Endoleaks with Onyx. J. Vasc. Interv. Radiol. vol. 12 629-632 Vancouver May 2001.
Adrian J. Ling et al. (2007) Treatment of a Large Type II Endoleak Via Extraperitoneal. J. Vasc. Interv. Radio. vol. 18 659-662 AUS. May 2007.
Mario Zanchetta et al. 2007 Intraperative Intrasac Thrombin Injection to Prevent Type II. J. Endovasc. Their vol. 14 176-783 Italy Apr. 2007.
Jean Raymond et al. (2002) In Situ Beta Radiation to Prevent Recanalization After Coil. Stroke Vo. 33 421-427 Montreal Feb. 2002.
Timothy A.M. Chuter et al. (2001) Endoleak After Endovascular Repair of Abdominal Aortic Aeurysm. Journal of Vascular Surgery vol. 34 No. 1, 98-105 California Jul. 2001.
Caroline D. Hoemann et al. (2005) Chitsan-Glycerol Phosphate/ Blood Implants Improve Hyaline Cartillage. Journal of Bone & Joint Surgery Inc. Vo. 87, 2671-12686 Montreal Dec. 2005.
T. Fuchs et al. (1997) Gel Point in Physical Gels: Rheology and Light Scattering. Elsevier Science 5, 541-559 Germany May 1997.
H.H. Winter 1987 Can the Point of a Cross-linking Polymer. Polymer Engineering and Science vol. 27 No. 22, 1698-1702 Massachusetts Dec. 1997.
Jade S. Hiramoto et al. (2007) Long-Term Outcome and Reintervention After Encovascular. Journal of Vascular Surgery 461-466 Mar. 2007.
Dare Mutiyu S et al. 2006 Midterm Follow-up of a Single-Center. J. Vasc Interv. Radiol. vol. 17, 973-977 UK Jun. 2006.
I.E. Steinbruber et al (2006) Technical and Clinical Success of Infrarenal. European Journal of Radiology. Vo. 59, 384-392 Austria Apr. 2006.
S.M. Thomas et al. (2005) Results From the Prospective Registry. J. Vasc. Endovvasc Surg. vol. 29, 563-570 UK Jun. 2005.

(Continued)

*Primary Examiner* — Micah-Paul Young
(74) *Attorney, Agent, or Firm* — Brinks Gilson & Lione

(57) ABSTRACT

A sclerosing embolizing hydrogel comprising from about 0.1% by weight to about 4.0% by weight of chitosan; from about 0.01M to about 1M of hydrochloric acid; from 0% by volume to about 40% by volume of iopamidol; from 0.5% by weight to about 25% by weight of β-glycerophosphate disodium salt; and from about 0.05% by weight to about 4% by weight of sodium tetradecyl sulphate. Also a kit for synthesizing the hydrogel and a method using the hydrogel to treat a vascular defect in a subject.

9 Claims, 6 Drawing Sheets

(56) References Cited

OTHER PUBLICATIONS

David C. Brewster et al. 2006 Long-Term Outcomes After Endovascular Abdominal. Annals of Surgery vol. 244 No. 3, 426-438 Boston Sep. 2006.
Frank J. Veith et al. (2002) Nature and Significance of Endoleaks. Journal of Vascular Surgery vol. 35 No. 5, 1029-1035 Pennsylvania May 2002.
Evar Trial Participants* (2005) Endovascular Aneurysm Repair and Outcome in Patients. The Lancet.com. vol. 365, 2187-2191 Jun. 2005.
Jan D Blankensteijn et al. (2005) Two-Year Outcomes After Conventional of Endovascular. The New England Journal of Med. 352 No. 23, 2398-2405 Massachusetts Jun. 2005.
G.A.J. Frasen et al. (2003) Rupture of Infra-Renal Aortic Aneurysm. Eur. J. Vasc. Endovasc Surg. vol. 26, +487-493 Liverpool Nov. 2003.
Peter L. Harris et al. (2000) Incidence and Risk Factors of Late Rupture Conversion. Journal of Vascular Surgery, vol. 32 No. 4. 739-749 US Oct. 2000.
K. Tiessenhaussen et al. (2005) Surgical Conversion of Abdominal Aortic. Eur. J. Vasc. Endovasc Surg. vol. 31, 36-41 Austria Aug. 2005.
Giovanni Torsello et al. 2006 Long-Term Outcome After Talent Endograft Implantation. Journal of Vascular Surgery vol. 43 No. 3, 277-284 Germany Feb. 2006.
Corinne Van Marrewijk (2002) Significance of Endoleaks After Endovascular Repair. Journal of Vascular Surgery, vol. 35, 461-473 The Netherlands Mar. 2002.
Jason Y. Rhee et al. (2005) Treatment of Type II Endoleaks with a Novel Polyurethane. Journal of Vascular Surg. vol. 42 No. 2, 321-328 US Aug. 2005.
R. Uflacker,, T. Brothers 2006 Filing of the Aneurysmal Sac With Deac-Glucosamine. The Journal of Cardiovascular Surg. vol. 47 No. 4, 425-436 Carol. South Aug. 2006.
L. Joseph Melton et al. (1983) Changing Incidence of Abdominal Aortic. The Journal of Infectious Diseases vol. 120 Issue 3.379-386 US Jul. 1983.
Annals of Internal Medicine vol. 134 No. 3, 182-190 US Feb. 2001 Anne B. Newman et al. (2001) Cardiovascular Disease and Mortality in Older Adults.
Monique Prinssen et al. (2004) A Randomized Trial Comparing Conventional and Endovascular. The New England Journal of Med. 351 No. 16, 1607-1618 Massachusetts Oct. 2004.
The Eviar Trial Participants* 2004 Comparison of Endovascular Aneurysm Repaid with Open Repair in Patients. The Lancet.com vol. 364, 843-848 UK Sep. 2004.
Current Interpretation of the UK Evar Trials R.M. Greenhalgh et al. ACTA Chir Belg. Belsurg. Belgian Surgical Website vol. 106, 137-138 UK Apr. 2010.
Ganji et al., Gelation time and degradation rate of chitosan-based injectable hydrogel, J Sol-Gel Sci Techn, 2007, vol. 42, pp. 47-53.
Sotradecol from Bioniche Pharma Group Limited dated Oct. 2004.
Michael L. Martin, M, et al., Treatment of Type II Endoleaks with Onyx, May 2001 JVIR, vol. 12, No. 5, pp. 629-632.
R. M. Greenhalgh, et al., Current Interpretation of the UK EVAR Trials, ACTA Chirurgica Belgica No. 2, Mar.-Apr. 2006, pp. 136-138.

* cited by examiner

EMBOLIZING SCLEROSING HYDROGEL

The present application is a division of U.S. patent application Ser. No. 13/112,289, filed May 20, 2011 which claims priority from U.S. Provisional Patent Application Ser. No. 61/344,089 filed May 20, 2010, the contents of which is are hereby incorporated by reference in their entirety.

FIELD OF THE INVENTION

The present invention relates to the art of medical treatments. More specifically, the present invention is concerned with an embolizing sclerosing hydrogel and its applications in treatments of vascular defects.

BACKGROUND

Endovascular aneurysm repair is an alternative to surgical repair of abdominal aortic aneurysm which enables to reduce patient operating risks and time of recovery. However, this treatment is presently limited by the persistence of blood leaks (called endoleaks). Some of these endoleaks (type II endoleaks) can be treated by injecting an embolizing agent to block blood flow.

Several embolizing agents (mainly N-butyl-2-cyanoacrylate (NBCA) [1-4], Ethylenevinyl alcohol copolymer (EVOH, Onyx® [5, 6], polyurethane fragments and fibrin glue [7], combined or not with coils [4, 8]) have been tested recently for the treatment of endoleaks or for their prophylactic prevention by injection into the aneurismal sac. Although these studies showed that sac embolization has potential to minimize endoleak occurrence, they also show that materials existing presently are limited. Recurrence of endoleaks are frequent. It is believed to be due to recanalisation process through or around the injected materials. The same limitation occurs when prophylactic injection of embolizing agent around the implant is performed in order to prevent endoleak formation [3, 9, 10]. It is believed that combining embolizing and sclerosing properties would improve clinical results by inducing endothelial denudation and thus preventing recanalisation processes and promoting fibrosis and healing. The only commercialized embolizing agent that may present sclerosing properties to date is cyanoacrylate. However this agent is not biodegradable and such embolizing agent do not exist presently or they do not present adequate mechanical and biodegradation properties.

In the case of arteriovenous malformation, sclerosing agents such as ethanol and sodium tetradecyl sulphate foams are already used to permanently occlude the vessels. However, these agents are far from ideal since their poor mechanical properties make injection difficult to control and do not enable to efficiently occlude blood flow.

Endovascular aneurysms repair (EVAR) clinical outcome is severely limited by the persistence of blood flow perfusing the aneurysm, called endoleaks, observed in 10% to 36% of cases [14-17]. The most frequent type of endoleak is type II endoleak, which corresponds to retrograde flow from collateral arteries [18, 19]. Persistent type II endoleaks with sac size progression require interventions as they can lead to aneurysm rupture [14, 15, 17, 18, 20-26]. Several attempts have been recently made to treat or prevent type II endoleaks using coils or polymeric embolising agents (mainly N-butyl-2-cyanoacrylate (NBCA) [1-4], Ethylenevinyl alcohol copolymer (EVOH, Onyx® [5, 6], polyurethane fragments [27] and fibrin glue [7], combined or not with coils [4, 8]. These studies showed that sac embolization has potential to minimize endoleak occurrence. However, embolization failure (recurrence, recanalisation) was reported with all tested agents. Prophylactic embolization of the inferior mesenteric and/or lumbar arteries or of the entire aneurismal sac during EVAR has also been proposed in patients to prevent endoleak formation, once again with limited success [3, 9, 10]. Uflacker et al. reported a high proportion of residual leaks in an animal model despite deacetylated glucosamine injection into the aneurysm [28]. In a human study, injection of fibrin glue decreased the rate but did not completely prevent type II endoleaks (2.4%) [7]. Injectable agents developed to date are not only unable to treat or prevent all endoleaks. They are also far from ideal for such clinical use. Cyanoacrylate and Onyx are difficult to control during injection, are non-biodegradable and non porous, thus preventing tissue healing in the cast. Their long-term biocompatibility is questionable. Moreover they are also very radiopaque and could create a diagnostic challenge in surveillance imaging studies. The two components of fibrin glue must be injected separately and cannot easily fill up the cavity, since they immediately form a blood clot.

Accordingly, there is a need in the industry to provide a gel for repairing aneurysms and other vascular defects. An object of the present invention is therefore to provide such a gel.

SUMMARY OF THE INVENTION

In a broad aspect, the invention provides a sclerosing embolizing hydrogel comprising: from about 0.1% by weight to about 4.0% by weight of chitosan; from about 0.01M to about 1M of an acid; from 0.5% by weight to about 25% by weight of β-glycerophosphate disodium salt; and from about 0.05% by weight to about 4% by weight of sodium tetradecyl sulphate.

In some embodiments of the invention, the acid is selected from the group consisting of: acetic acid, ascorbic acid, salicylic acid, phosphoric acid, hydrochloric acid, propionic acid, formic acid, lactic acid and mixtures thereof. In a very specific embodiment of the invention, the acid is hydrochloric acid.

In some embodiments of the invention, the hydrogel has a pH of from about 7 to about 7.4. This pH is physiological and advantageous for injection in the human body.

In some embodiments of the invention, the hydrogel further comprises an imaging contrast agent. For the purpose of this document an imaging contrast agent is a substance that improves the visibility of the hydrogel when using a medical imaging device when compared to a situation in which the contrast agent is not present in the hydrogel. For example, the imaging contrast agent is a radiopaque substance, but other types of contrast agent are within the scope of the present invention. For example, the imaging contrast agent is a radiopaque substance. In some embodiments of the invention, the imaging contrast agent is selected from the group consisting of: Hypaque Meglumine, Reno, Conray, Renografin, Hypaque Sodium, Hexabrix, Oxilan, iohexol (Omnipaque), iopamidol (Isovue), iopromide (Ultravist), ioversol (Optiray), iodixanol (Visipaque), iothalamate (Conray) and ioxaglate (Hexabrix). Iohexol (Omnipaque), iopamidol (Isovue), iopromide (Ultravist) and ioversol (Optiray) are non-ionic monomers. Iodixanol (Visipaque) is a non-ionic dimer. Iothalamate (Conray) is an ionic monomer. Ioxaglate (Hexabrix) is an ionic dimer. The proposed hydrogel is therefore usable with a wide range of divers imaging contrast agents.

In a specific embodiments of the invention, the imaging contrast agent is iopamidol. For example, the hydrogel comprises from 0% by volume to about 40% by volume of iopamidol.

In some embodiments of the invention, the hydrogel has a storage modulus of from about 1 kPa to about 10 kPa. This storage modulus is as measured when the hydrogel is completely gelled. Hydrogels having these properties are useful in many medical applications.

In some embodiments of the invention, the chitosan has a degree of deacetylation of from about 80% to about 95%. In some specific embodiments of the invention, the chitosan has a degree of deacetylation of from about 80% to about 85%. This percentage has been found to be optimal for biodegradation of the hydrogel for certain procedures. Indeed, adjusting suitably the degree of deacetylation allows for an adjustment of the biodegradability of the hydrogel, and therefore influences its rate of disappearance in the body.

In some embodiments of the invention, the hydrogel includes from about 1% by weight to about 3% by weight of sodium tetradecyl sulphate. While this interval is strictly supported by experimental data presented hereinbelow, the larger interval for the concentration of STS given hereinabove is thought to be achievable with useful mechanical properties in view of the experiments that were performed.

In a specific embodiment of the Invention, the hydrogel includes about 2% by weight of chitosan; about 0.1M of hydrochloric acid; about 12% by weight of β-glycerophosphate disodium salt; about 1% by weight of sodium tetradecyl sulphate; and about 20% by volume of iopamidol.

In another specific embodiment of the invention, the hydrogel includes: about 2% by weight of chitosan; about 0.1 M of hydrochloric acid; about 10% by weight of β-glycerophosphate disodium salt; about 3% by weight of sodium tetradecyl sulphate; and about 20% by volume of iopamidol.

In another broad aspect, the invention provides a kit for synthesizing a sclerosing embolizing hydrogel, the kit comprising: a first container containing chitosan in an acid solution; and a second container containing β-glycerophosphate disodium salt and sodium tetradecyl sulphate.

In some embodiments of the invention, the first container also contains an imaging contrast agent. In some embodiments of the invention, the kit further comprises a mixer for mixing the contents of the first and second containers. In some embodiments, the second container contains an aqueous solution in which β-glycerophosphate disodium salt and sodium tetradecyl sulphate are dissolved. In other embodiments, the β-glycerophosphate disodium salt and sodium tetradecyl sulphate are provided in any other suitable manner.

In another broad aspect, the invention provides a method for treating a vascular defect in a subject, for example a non-human mammal or a human, the method comprising implanting at an implantation site in the subject the hydrogel as defined hereinabove. For the purpose of this document, the terminology vascular defect relates to a vascular structure that requires an alteration.

In some embodiments of the invention, the vascular defect is selected from the group consisting of: an aneurysm, an abdominal aortic aneurysm and a vascular anomaly. In some examples, the vascular defect is an endoleak after endovascular aneurysm repair. In other examples, the vascular defect is a vascular anomaly selected from the group consisting of an arteriovenous malformation, a venous malformation, a lymphatic malformation, an hemangioma, a varicocele and pelvic congestion syndrome.

In some embodiments of the invention, the implantation site is substantially adjacent the vascular defect.

In some embodiments of the invention, the method uses a catheter defining a catheter proximal end and an opposed catheter distal end. Implanting the hydrogel includes: inserting the catheter in the subject with the catheter distal end positioned substantially adjacent the implantation site and the catheter proximal end provided outside of the subject; mixing precursor solutions of the hydrogel outside of the catheter to form a mixed hydrogel forming solution and injecting the hydrogel forming solution through the catheter at the implantation site. The hydrogel is thus implanted at the implantation site. For the purpose of this document, the terminology hydrogel forming indicates a solution that is in process of gelation or which has completed this process.

In some embodiments of the invention, the method further includes stenting the vascular defect before injecting the hydrogel forming solution. In some embodiments of the invention, the method further includes excluding blood flow at the implantation site before injecting the hydrogel forming solution.

The present invention relates to a new injectable embolizing material with sclerosing properties. While many uses for the hydrogel have been described hereinabove, such material could also be used to treat other pathologies, such as for the treatment of cancer.

Many pathologies require embolizing treatments but materials existing presently do not lead to satisfactory results. The proposed hydrogel is a new embolizing material based on a new paradigm and which has unique properties enabling a safe, efficient and durable embolization.

The terminology "about" as used in this document qualifying a quantity refers to small variations in the numerical value qualified that would not affect the physical and chemical properties of the proposed hydrogel in a significant manner, as appreciated by a person skilled in the art.

The present application cites many documents, the contents of which is hereby incorporated by reference in their entirety.

Other objects, advantages and features of the present invention will become more apparent upon reading of the following non-restrictive description of preferred embodiments thereof, given by way of example only with reference to the accompanying drawings.

DETAILED DESCRIPTION

The present invention relates to the development of an embolizing agent with sclerosis properties which combines appropriate mechanical, biocompatibility, biodegradation and gelation properties for such applications. The hydrogel created is based on chitosan, a biocompatible biodegradable biomaterial and sodium tetradecyl sulphate (STS), a sclerosing agent. Methods were developed to create an embolic sclerosing hydrogel which does not precipitate, has superior mechanical properties and enables controlled injection.

The present invention relates to an embolic hydrogel with sclerosing properties. The composition of this hydrogel is:
Chitosan (CH).
β-glycerophosphate (βGP).
Sodium tetradecyl sulphate (STS).
Depending on the desired application, the hydrogel can be created radiopaque or not, by addition of a contrast agent such as Iopamidol (or others). Radiopacity is important in some treatments of abdominal aortic aneurysms. It is sometimes not required for some vascular malformations. Also, it is contemplated to use other imaging contrast agents for augmenting the contrast of the hydrogel using other imaging modalities.

Figure 1:
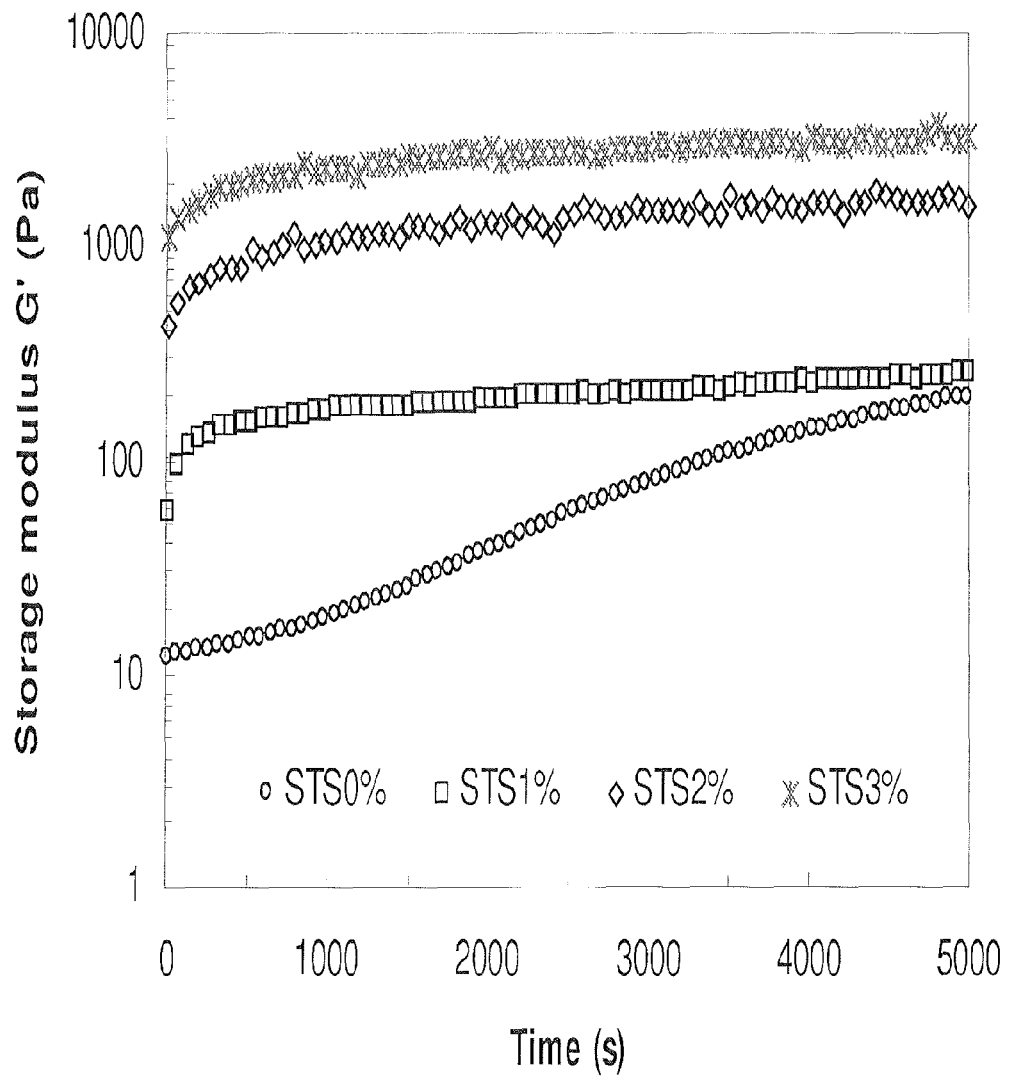
FIG. 1, in an X-Y graph illustrates the time dependence of storage modulus (G') of a radiopaque hydrogel in accordance with an embodiment of the invention as a function of sodium tetradecyl sulphate (STS) concentration (0, 1, 2 and 3% w/v) at 37° C, increasing concentrations of STS providing an improvement in rheological and mechanical properties for embolization.

The unique combination of chitosan, βGP and STS enables to create an embolic sclerosing hydrogel with good mechanical properties, that can be injected easily and has immediate mechanical properties adequate for embolization, as illustrated in FIG. 1. The addition of a contrast agent such as Iopamidol does not prevent gelation and only slightly increases its final mechanical properties.

Figure 2:
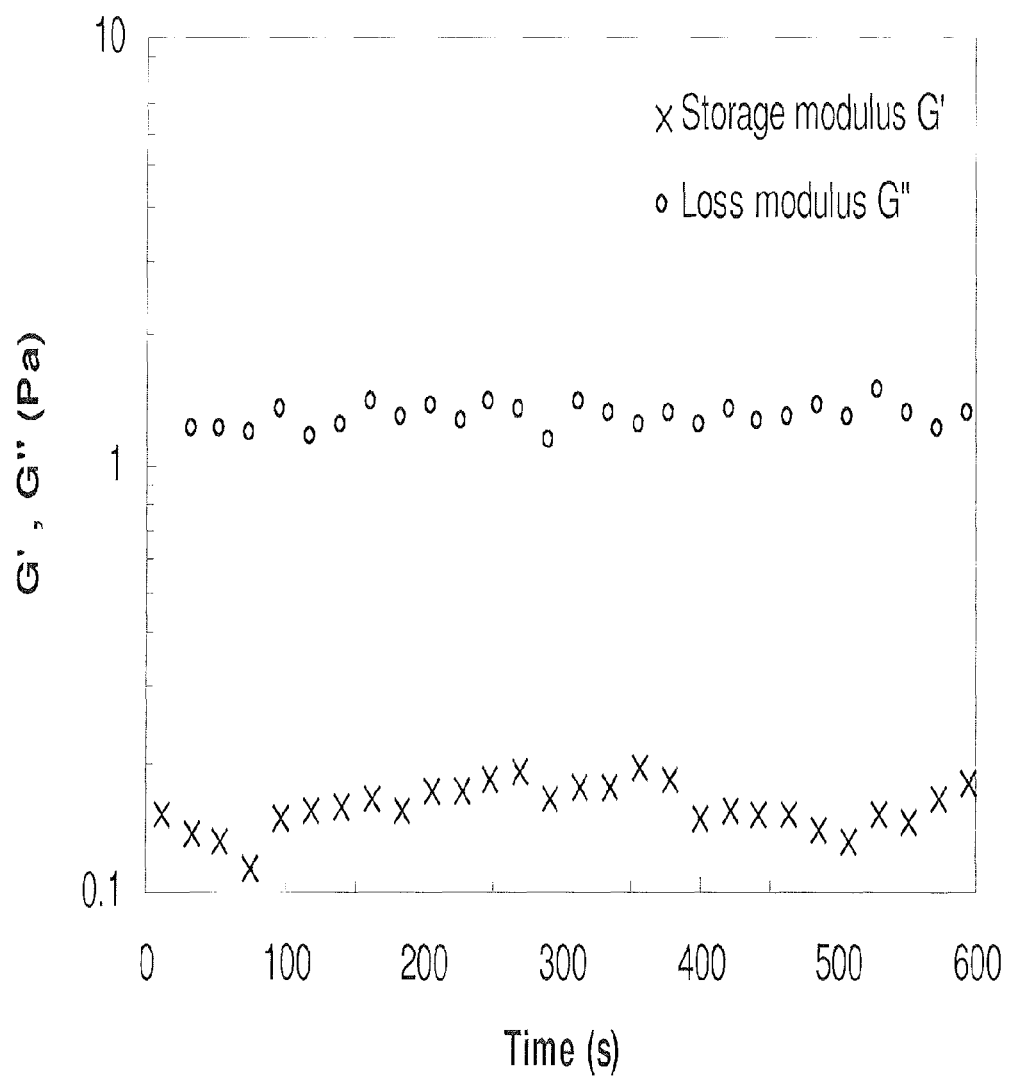
FIG. 2, in an X-Y graph, illustrates the time dependence of storage (G') and loss (G") moduli of a radiopaque STS solution (20% v/v iopamidol (IOP), 3% w/v STS, without chitosan hydrogel) at 37° C., a viscous liquid behavior being observed without any rigid mechanical properties.

The unique association of chitosan, βGP and STS provides more appropriate rheological and mechanical properties compared to chitosan+ βGP (FIG. 1) or to STS alone, which is liquid (FIG. 2). It is also possible to create an hydrogel that has many properties suitable for medical treatment, such as a physiological pH, for example between 7.0 and 7.4.

The addition of βGP enables to add STS to chitosan without inducing its precipitation. The procedure of fabrication itself (pH of each component before mixing and the order of addition) is important to avoid precipitation or phase separation of chitosan at physiological pH, as shown in Table 1.

The proposed hydrogel is an elastic material (G'>1000 Pa), as compared to STS foam (viscous material) that is presently used in the treatment of arteriovenous malformations (FIG. 2).

Figure 3:
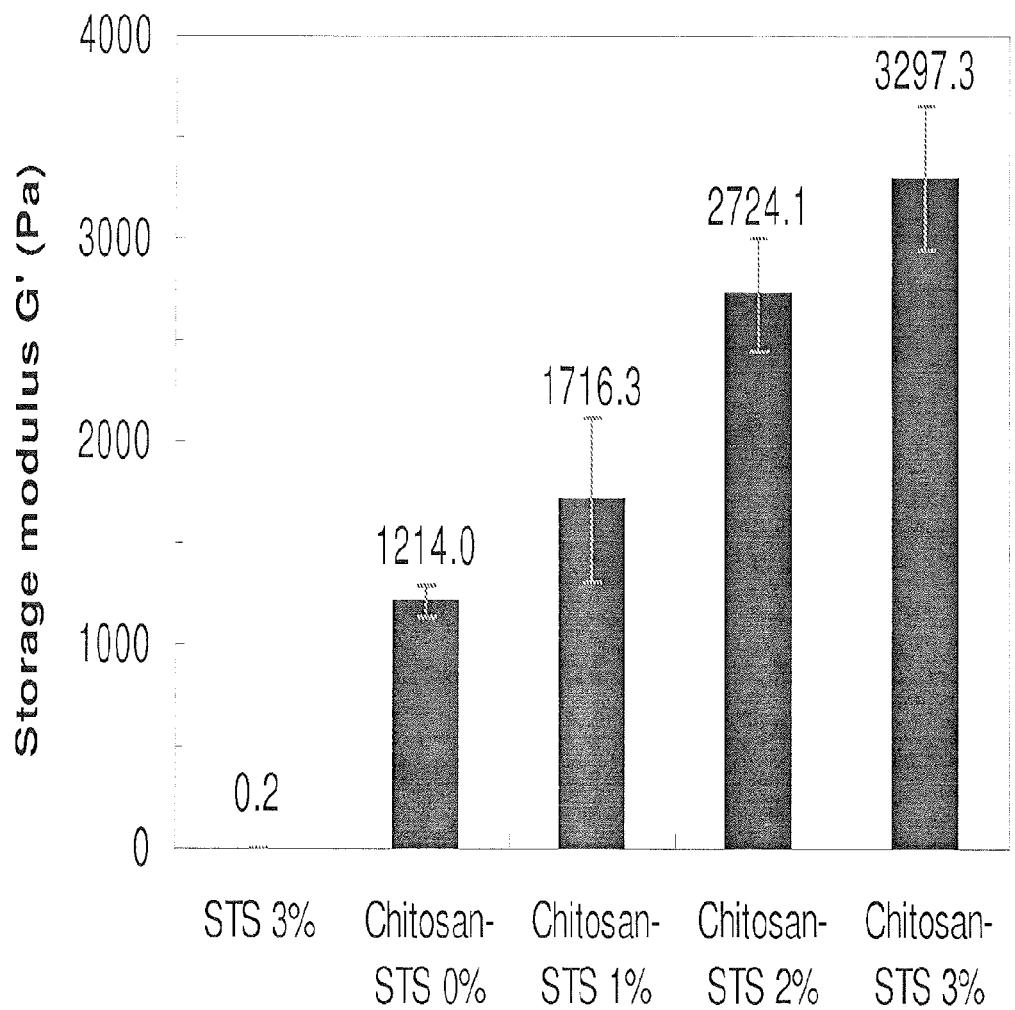
FIG. 3, in a bar chart, illustrates the storage modulus (G') of radiopaque chitosan hydrogel (2% w/v chitosan (CH), 20% v/v IOP, 12% w/v β-glycerophosphate (βGP) obtained after 1 week of gelation at 37° C. as a function of STS concentration (0, 1, 2 and 3% w/v), showing that the storage modulus is increased after 1 week as a function of STS concentration, thus enabling better embolization properties, the present invention solving many problems inherent in the art as the chitosan/STS hydrogel is much stronger than the STS (3%) foam and can displace the blood into aneurysm more effectively.

The proposed hydrogel increases the storage modulus of chitosan+βGP hydrogels, thus enabling better embolization properties, as illustrated in Table 2. For example, just after mixing, G' of chitosan+βGP is around 10 Pa compared with chitosan/STS (1357 Pa). After 1 week of gelation at 37° C., G' of chitosan+βGP is 1213 Pa compared with chitosan/STS (3297 Pa) (FIG. 3).

The proposed hydrogel adds sclerosing properties to chitosan, which prevents recanalisation processes and promotes fibrosis (healing).

Figure 4:
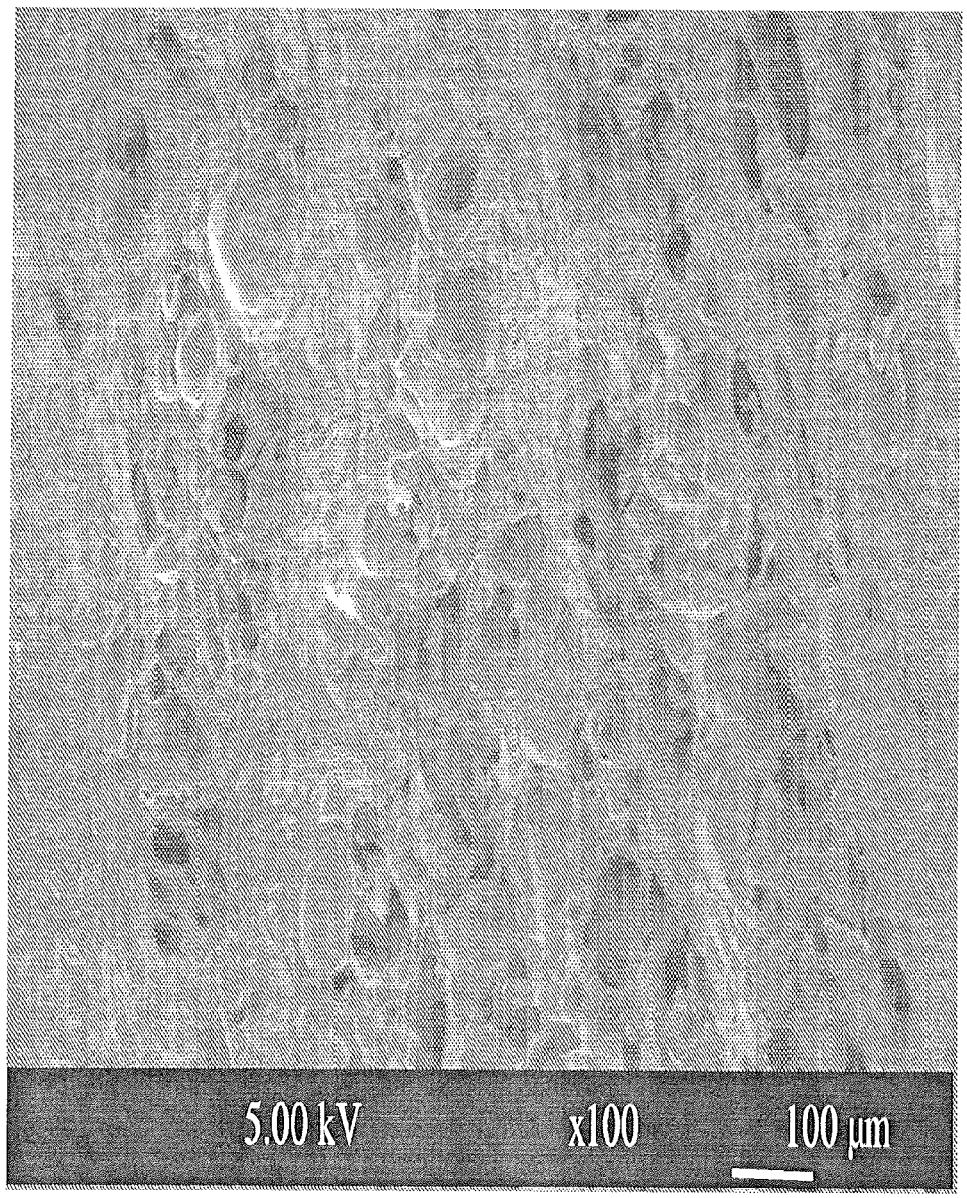
FIG. 4, in a photograph, illustrates the porous structure of the chitosan/STS hydrogel (2% w/v CH, 20% v/v IOP, 12% w/v βGP, 3% w/v STS), as observed by scanning electron microscopy after gold sputtering.

The hydrogel is a porous matrix appropriate for cell invasion during healing process, as shown in FIG. 4.

The hydrogel can be become radiopaque by addition of a non-ionic contrast agent (for example at 20% v/v) which does not significantly modify its gelation or mechanical properties. The contrast agent is simply entrapped in the hydrogel and is rapidly eliminated and thus does not to interfere with further imaging follow-up.

If required, the two solutions required to create the chitosan/STS hydrogel can be sterilized before mixing and the chitosan/STS hydrogel is considered as a ready-to-use biomaterial. Indeed, the proposed hydrogel can be provided as a kit in which a first container a first container contains chitosan in an acid solution and a second container containing β-glycerophosphate disodium salt and sodium tetradecyl-sulphate. In some embodiments, the first container also contains an imaging contrast agent. The containers contain sufficient quantities of materials at proper concentrations to synthesize an hydrogel for the application for which it is intended in sufficient quantity.

The two solutions used to create the hydrogel can be mixed in the operating room, using a suitable mixer, and then injected via catheter without significant damage on its mechanical properties.

The proposed hydrogel is believed to be the first product with sclerosing properties proposed to treat endoleaks or do prophylactic prevention of endoleaks in abdominal aortic aneurysms. The two principle roles of the chitosan/STS hydrogel are the embolization of aneurysm sacs or other structures (to block any blood flow entering the aneurysms) and to cause an irreversible endothelial injury in the aneurysm sac (or other structure) to prevent recanalisation process by endothelial cells that could lead to recurrence of blood flow after a while, this process being thought to be a cause of failure of presently used embolic treatments.

Such an embolic sclerotic agent has a large commercial potential for the treatment of endoleak or for their prophylatic prevention by injection just after stent-graft (SG) deployment. The proposed hydrogel has many advantages compared to presently used agents (mainly Histoacryl (cyanoacrylate) and Onyx (polyvinyalcool mixed with dimethyl sulfoxide (DMS), Embogel (Alginate mixed with calcium chloride). Indeed:

1) The hydrogel's sclerosing effect is well controlled. STS is an anionic surfactant that has been demonstrated to destroy endothelial lining in vivo. It is commonly used in sclerotherapy. Its combination with the cationic chitosan limits its diffusion during the EVAR procedure and thus decreases safety risks. It can be added at any concentrations, based on clinical data). In Onyx, DMSO can also have a sclerosing effect. Yet DMSO is liquid and can be easily release in surrounding tissues.

2) Gelation of chitosan/STS was found to be adequate to allow easy clinical handling, positioning and injection while limiting risks of migration in vivo. The rapid increase of storage modulus avoids risks of migration but does not require to be mixed in vivo as other products, nor create risk of catheter adhesion in vivo. In contrast, rapid polymerisation of cyanoacrylate can lead to catheter obstruction and sticking into the treated arteries.

3) The mechanical properties of the proposed hydrogel (above 1000 Pa after gelation) are sufficient for flow occlusion in the aneurismal sac but its viscosity allows it to easily fill and mold to any shape or defect in vivo (in contrast to cyanacrylate that often lead to empty spaces).

4) Chitosan is biocompatible and biodegradable. It forms a porous matrix which can be infiltrated and progressively replaced by tissue, thus not impairing the healing process after EVAR [11] in contrast to permanent Onyx and cyanoacrylate that are permanent.

5) Chitosan/STS is also biodegradable. After injection in the rabbit auricular artery, chitosan/STS prepared with chitosan 83% DDA was shown to be replaced by fibrous tissue within 1 month. The degree of deacetylation (DDA) of chitosan can be modified to modify the degradation rate.

6) Chitosan is hemostatic and may thus favour thrombosis in the aneurismal sac [11]. It is muco-adhesive, and by binding with surrounding tissues, should allow good flow occlusion and limit migration.

The addition of β-glycerophosphate salt allows to avoid precipitation of chitosan before its gelation in a viscoelastic hydrogel. Addition of sodium tetradecyl sulphate increases the gelation rate and leads to better mechanical properties compared to chitosan alone, as characterized by rheometry (FIG. 3). This allows good embolization properties in vivo, as assessed on efficient embolization of renal artery, as described hereinbelow.

EXAMPLE

Materials & methods

Materials

Medium molecular weight (Mw) chitosan (Mw~4.2×105 Da) with a relatively high degree of deacetylation (DDA~83%) and β-glycerophosphate disodium salt hydrate (βGP) were used in this study. Chitosan with other DDA could be used alternatively to modify the degradation rate. The imaging contrast agent used in this study was iopamidol (IOP) from Bracco Diagnostics Inc. (Canada) but other liquid iodinated contrast agents can also be used. Also, in other embodiments of the invention, other suitable imaging contrast agents are usable. Sodium tetradecyl sulphate (STS), dibasic sodium phosphate, monobasic sodium phosphate and hydrochloric acid were acquired from Sigma-Aldrich (Canada).

Preparation of STS Solution at Physiological pH

Different STS solutions were prepared at different concentrations by diluting STS solution (27% w/v) until an appropriate volume of dibasic sodium phosphate/monobasic sodium phosphate was obtained.

Preparation of Radiopaque Chitosan Hydrogel with Sclerosing Properties: Chitosan/STS A chitosan solution was prepared by dissolving chitosan powder in 0.1 M HCl with an appropriate amount of iopamidol at room temperature under constant magnetic stirring. The sample was sterilized at 121° C. for 20 min and stoked at 4° C. for 24 h. βGP-STS solutions were prepared by dissolving an appropriate amount of βGP powder in STS solution. The βGP-STS solution was then sterilized using a 0.2 μm filter. The βGP/STS solution was mixed with chitosan solution to form the radiopaque chitosan hydrogel at 37° C. with sclerosing properties (chitosan/STS).

Rheologlcal Measurements

Rheological measurements were performed using the Bohlin CVO rheometre (Malvem Instruments Inc., USA) equipped with co-axial cylinder or parallel-plate geometry and a circulating water bath to control the temperature. Rheologlcal data were collected using the Bohlin software. Small-amplitude oscillatory shear experiments were performed at 37° C. The time evolution of storage (or elastic) modulus G' and loss (or viscous) modulus G" was determined within the linear viscoelastic region, at fixed frequency (1 Hz) and stress amplitude (1 Pa). The time dependence of G' and G" of chitosan hydrogels were measured as a function of STS concentration. The gelation time ($t_{gel}$) was then determined as the time at which G'=G" in accordance with the approach proposed in the literature [12, 13]. The study was performed in triplicate.

Swelling Properties

Figure 5:
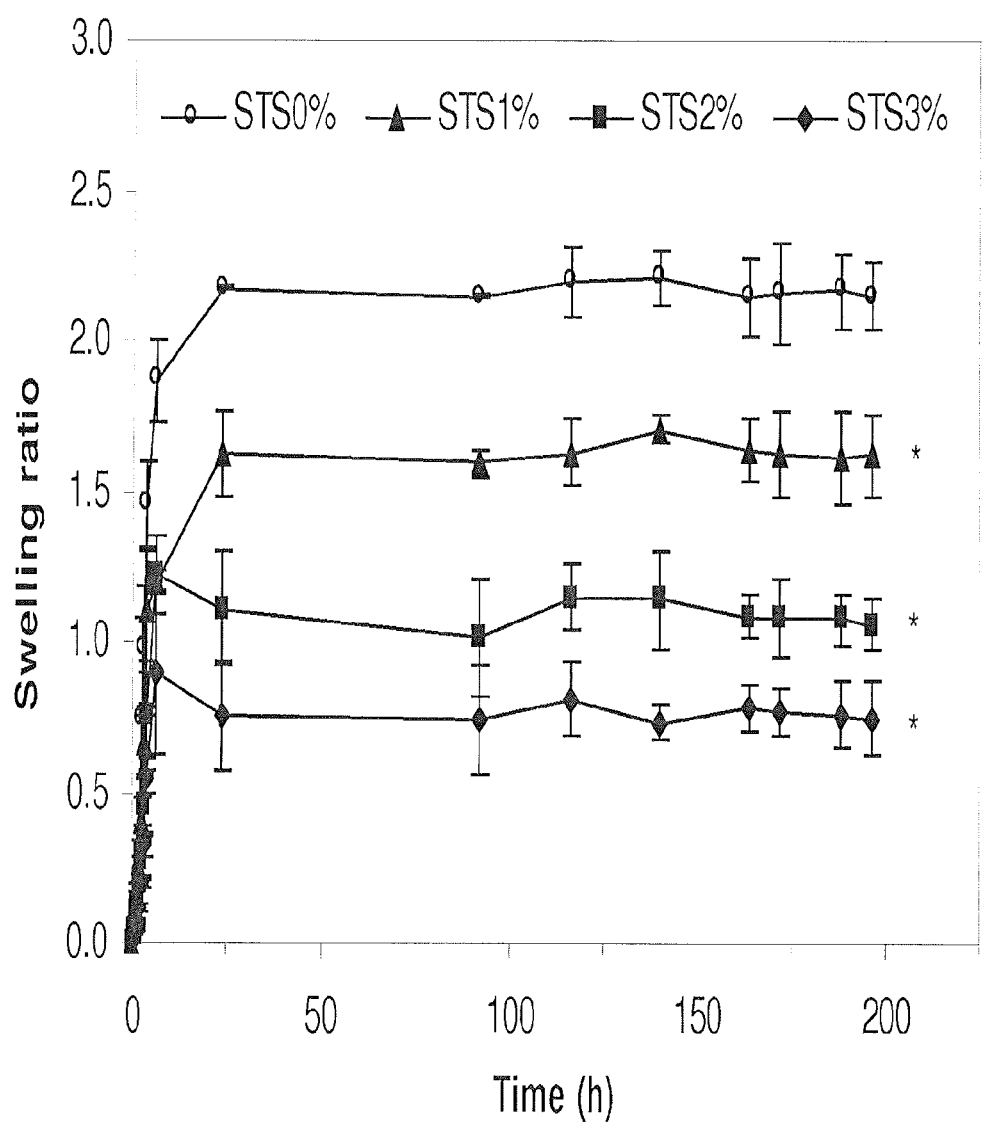
FIG. 5, in an X-Y graph, Illustrates the swelling properties as a function of STS concentrations (2% w/v CH, 12% w/v βGP, 20% v/v IOP) of chitosan hydrogel immersed in PBS buffer at 37° C., where an * indicates a significant differences (p<0.05) of swelling equilibrium obtained after 8 days compared to chitosan hydrogel.

After the hydrogel reached gelation equilibrium (1 week of gelation at 37° C.), the degree of swelling was determined by keeping lyophilized specimens in phosphate buffer solution (pH 7.4) at 37° C. and recording variations in their weight in comparison to their initial weight ($W_0$). At regular time intervals, the hydrogels were weighed ($W_t$) and medium was changed. The swelling ratio ($S_w$) of hydrogels was calculated using the following equation:

$$S_w = \frac{W_t - W_0}{W_0}$$

where $W_t$ and $W_0$ are the weights of the water-swollen samples and the initial lyophilized hydrogel samples, respectively. The study was performed in triplicate. Results are shown in FIG. 5.

Morphology of Chitosan/STS Hydrogels

The morphology of chitosan/STS hydrogels was observed by scanning electron microscopy (SEM). After 1 week of gelation at 37° C., the prepared specimens were freeze-dried under vacuum during 24 h and sputter-coated with gold, and their morphology was observed. As chitosan hydrogels, chitosan-STS hydrogels were shown to exhibit a porous structure, as seen in FIG. 4.

In vivo Testing of Chitosan/STS Hydrogels

Chitosan/STS hydrogels were tested in vivo in various studies.

Rabbit artery model: The objective of this experiment was to investigate if embolization with chitosan/STS can prevent endothelial recanalization in a rabbit auricular artery (AA) model. Each AA was canulated and injected with 0.6 ml of chitosan (chitosan 2% w/v, iopamidol 20% v/v, BGP 12% w/v) (OCh; n=14) on one side and either saline (OSal; n=2), chitosan/STS 1% (chitosan 2% w/v, iopamidol 20% v/v, BGP 12% w/v, STS 1% w/v) (OCS1; n=6), or chitosan/STS 3% (chitosan 2% w/v, iopamidol 20% v/v, BGP 12% w/v, STS3% w/v) (OCS3; n=6) in the controlateral side (randomly assigned). All hydrogels were prepared and sterilized as described hereinabove. AA patency and percentage of recanalisation was assessed by visual inspection and Laser Doppler after embolization and at 1, 7, 14, and 30 days. The rabbits were sacrificed at 30 days to assessed endothelial ablation and inflammatory response by histological analyses. All AA's were catheterized and embolized with success. After 30 days, all the OSal were patent. Percentage of recanalization in comparison with initial embolization length were 25.6+/−34.4% in OCS1 (6+/−7 mm), and 22.5+/−15.9% in OCS3 (12+/−8 mm) without statistical difference with student test (p 0.05). At histology, chitosan/STS was shown to generate inflammatory response and was then replaced by fibrous tissue.

Canine model of aneurysms reproducing endoleaks after endovascular aneurysm repair with a stent-graft were created in 3 dogs. One endoleak was treated by chitosan/STS (chitosan 2% w/v, iopamidol 20% v/v, BGP 12% w/v, STS 3% w/v) and its controlateral control by chitosan (chitosan 2% w/v, iopamidol 20% v/v, BGP 12% w/v). All hydrogels were prepared and sterilized as described hereinabove. Chitosan/STS led to good control during embolization while chitosan hydrogel showed some migration into the collaterals. No migration into the stent-graft lumen was observed. One small leak was visible by angiography just after embolization but disappeared during the first week. At three months, no endoleak was detected while endoleak was present in ⅓ aneurysm treated with chitosan alone. In this challenging animal model, untreated endoleak persist in all aneurysms when left untreated.

While only some examples of hydrogels in accordance with the invention are provided, it is believed that a hydrogel according to the claims will have similar beneficial properties. Notably, it is believed, from the common knowledge present in the field of the invention and the experimental data obtained, that the following composition for the hydrogel would produce a useful hydrogel: from about 0.1% by weight to about 4.0% by weight of chitosan; from about 0.01M to about 1M of an acid; from 0.5% by weight to about 25% by weight of β-glycerophosphate disodium salt; and from about 0.05% by weight to about 4% by weight of sodium tetradecyl sulphate. Notably, while hydrochloric acid was used in this example, it is believed that at least for some applications for which the gel is intended, other acids such as acetic acid, ascorbic acid, salicylic acid, phosphoric acid, propionic acid, formic acid, lactic acid and mixtures thereof are usable.

Figure 6:
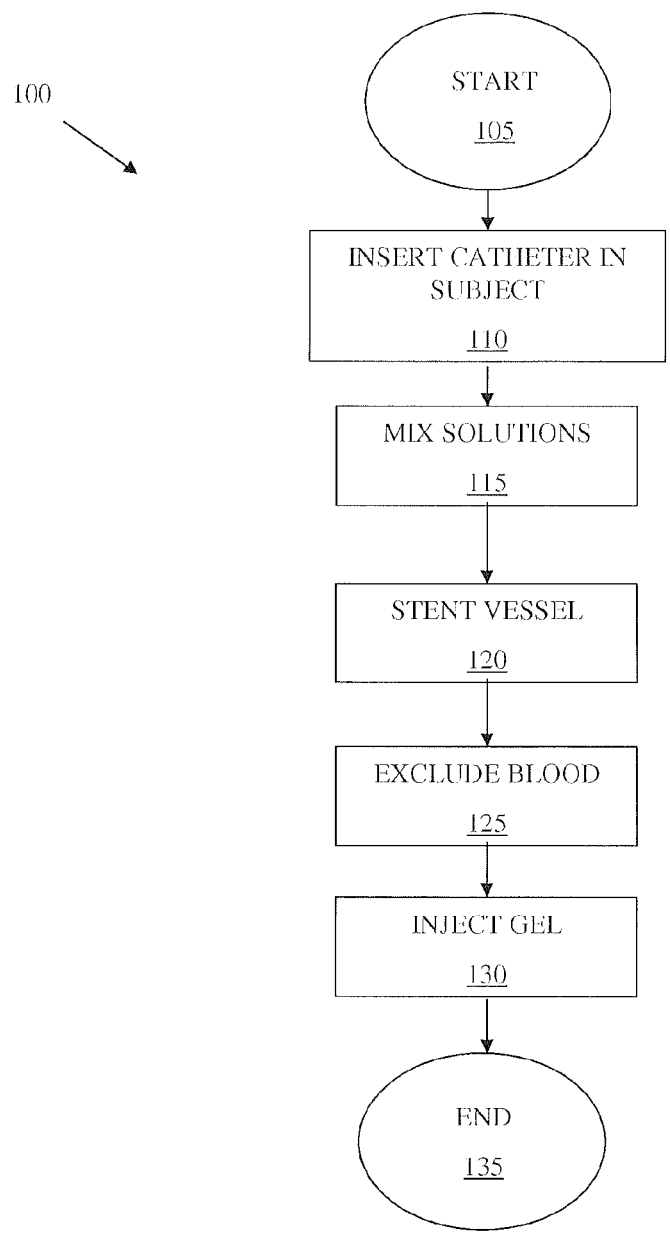
FIG. 6, in a flowchart, illustrates a method for treating a vascular defect in a subject in accordance with an embodiment of the present invention.

The above suggest an embolization procedure to treat aneurisms, other vascular defects and other pathologies and defects. The procedure is exemplified by the method 100 shown in FIG. 6. The embolization procedure is similar to that of other polymeric embolization agents such as Onyx and Histoacryl. For the prevention of endoleaks after EVAR, the agent could be easily injected at the time of the endovascular treatment by an angiographic catheter which would be placed into the aneurysm before stent-graft deployment Once the stent-graft is deployed, the aneurysm is excluded from blood flow and the agent can be safely injected into the aneurysmal sac.

To minimize risks of migration in collateral vessel, an occlusive balloon catheter can be deployed proximally in the vessel to avoid blood flow. The volume of the agent to be injected could be evaluated based on imaging data. Injection through a Glicath 4 French (Terumo, Tokyo, Japan) have been tested with success both in vitro and in vivo.

When an endoleak has been observed during stent-graft imaging follow-up, the agent can be used to treat the endoleak. In this case, the agent could be injected by a microcatheter (for example a 3 French catheter) positioned in the collateral vessel involved in the leak. It could also be injected by direct punction into the aneurysm (under CT scan or fluoroscopy). In this case, the agent is injected with a needle (for example 21 or 22 gage) then replaced by a micropunction system and a catheter or microcatheter. In this circumstances, only a small volume would be injected into the endoleak area.

For arteriovenous malformations or other treatments, the agent can be injected directly in the nidus by a needle, or using a catheter when necessary.

The proposed hydrogel is also usable in many other treatments, for example to treat varicose veins and cancer, the later, for example, by serving as a vehicle for a therapeutic agent. In addition, STS can act on blood irrigation of a tumor though its sclerosing properties, as well as acting on the tumor through these same properties. In these applications, the proposed hydrogel is used in replacement to hydrogels used in similar methods in the prior art.

More generally, the method 100 starts at step 105. The method uses a catheter defining a catheter proximal end and an opposed catheter distal end. At step 110, the catheter is inserted in a subject to treat with the catheter distal end positioned substantially adjacent an implantation site and the catheter proximal end provided outside of the subject.

Then, at step 115, precursor solutions of the hydrogel are mixed outside of the catheter to form a mixed hydrogel forming solution. An hydrogel forming solution is a solution in process of gelation, gelation can be partial or total prior to implantation in the subject, depending on the specific application contemplated. The precursor solutions includes the components of the hydrogel. For example, one of the precusor solution includes chitosan dissolved in HCl, and a second precursor solution includes βGP and STS.

At step 130 the hydrogel forming solution is injected through the catheter at the implantation site and the hydrogel is implanted at the implantation site, where gelation continues, if necessary. The method ends at step 135

In some embodiments, the method includes a step 120 of stenting the vascular defect before injecting the hydrogel forming solution. In some embodiments, the method also includes a step 125 of excluding blood flow at the implantation site before injecting said hydrogel forming solution, using conventional methods.

The order of some of the above-recited steps can be changed without departing from the scope of the invention, as the reader skilled in the art will readily appreciate.

Although the present invention has been described hereinabove by way of preferred embodiments thereof, it can be modified, without departing from the spirit and nature of the subject invention as defined in the appended claims.

REFERENCES

1. Raymond J, Berthelet F, Desfaits A C, Salazkin I, Roy D. Cyanoacrylate embolization of experimental aneurysms. AJNR Am J Neuroradiol 2002; 23:129-138.
2. Stavropoulos S W, Kim H, Clark T W, Fairman R M, Velazquez O, Carpenter J P. Embolization of type 2 endoleaks after endovascular repair of abdominal aortic aneurysms with use of cyanoacrylate with or without coils. J Vasc Interv Radiol 2005; 16:857-861.
3. Stavropoulos S W, Park J, Fairman R, Carpenter J. Type 2 endoleak embolization comparison: translumbar embolization versus modified transarterial embolization. J Vasc Interv Radiol 2009 October; 20(10):1299-1302.
4. Maldonado T S, Rosen R J, Rockman C B, Adelman M A, Bajakian D, Jacobowitz G R, et al. Initial successful management of type I endoleak after endovascular aortic aneurysm repair with n-butyl cyanoacrylate adhesive. J Vasc Surg 2003; 38:664-670.
5. Martin M L, Dolmatch B L, Fry P D, Machan L S. Treatment of type II endoleaks with onyx. J Vasc Interv Radiol 2001; 12:629-632.
6. Ling A J, Pathak R, Garbowski M, Nadkarni S. Treatment of a large type II endoleak via extraperitoneal dissection and embolization of a collateral vessel using ethylene vinyl alcohol copolymer (onyx). J Vasc Interv Radiol 2007; 18:659-662.
7. Zanchetta M, Faresin F, Pedon L, Ronsivalle S. Intraoperative intrasac thrombin injection to prevent type II endoleak after endovascular abdominal aortic aneurysm repair. J Endovasc Ther 2007; 14:176-183.

8. Raymond J, Leblanc P, Desfaits A C, Salazkin I, Morel F, Janicki C, et al. In situ beta radiation to prevent recanalization after coil embolization of cerebral aneurysms. Stroke 2002; 33:421-427.
9. Conrad M F, Adams A B, Guest J M, Paruchuri V, Brewster D C, LaMuraglia G M, et al. Secondary intervention after endovascular abdominal aortic aneurysm repair. Ann Surg 2009 September; 250(3):383-389.
10. Nevala T, Biancari F, Manninen H, Aho P S, Matsi P, Makinen K, et al. Type II Endoleak After Endovascular Repair of Abdominal Aortic Aneurysm: Effectiveness of Embolization. Cardiovasc Intervent Radiol 2009 Aug. 18.
11. Hoemann C D, Hurtig M, Rossomacha E, Sun J, Chevrler A, Shive M S, et al. Chitosan-glycerol phosphate/blood implants improve hyaline cartilage repair in ovine microfracture defects. J Bone Joint Surg Am 2005 December; 87(12):2671-2686.
12. Fuchs T, Richtering W, Burchard W, Kajiwara K, Kitamura S. Gel point in physical gels: rheology and light scattering from thermoreversibly gelling schizophyllan. Polym Gels networks 1997; 5:541-559.
13. Winter H H. Can the gel point of a cross-linking polymer be detected by the G-G crossover? Polym Eng Sci 1987; 27:1698-1701.
14. Hiramoto J S, Reilly L M, Schneider D B, Sivamurthy N, Rapp J H, Chuter T A. Long-term outcome and reintervention after endovascular abdominal aortic aneurysm repair using the Zenith stent graft. J Vasc Surg 2007 Jan. 23.
15. Seriki D M, Ashleigh R J, Butterfield J S, England A, McCollum C N, Akhtar N, et al. Midterm follow-up of a single-center experience of endovascular repair of abdominal aortic aneurysms with use of the talent stent-graft. J Vasc Interv Radiol 2006 June; 17(6):973-977.
16. Steingruber I E, Neuhauser B, Seiler R, Greiner A, Chemelli A, Kopf H, et al. Technical and clinical success of infrarenal endovascular abdominal aortic aneurysm repair: A 10-year single-center experience. Eur J Radiol 2006 September; 59(3):384-392.
17. Thomas S M, Beard J D, Ireland M, Ayers S. Results from the prospective registry of endovascular treatment of abdominal aortic aneurysms (RETA): mid term results to five years. Eur J Vasc Endovasc Surg 2005 June; 29(6):563-570.
18. Brewster D C, Jones J E, Chung T K, Lamuraglia G M, Kwolek C J, Watkins M T, et al. Long-term outcomes after endovascular abdominal aortic aneurysm repair: the first decade. Ann Surg 2006 September; 244(3):426-438.
19. Veith F J, Baum R A, Ohki T, Amor M, Adiseshiah M, Blankensteljn J D, et al. Nature and significance of endoleaks and endotension: summary of opinions expressed at an international conference. J Vasc Surg 2002 May; 35(5):1029-1035.
20. EVAR trial participants. Endovascular aneurysm repair and outcome in patients unfit for open repair of abdominal aortic aneurysm (EVAR trial 2): randomised controlled trial. Lancet 2005 Jun. 25-Jul. 1, 365(9478):2187-2192.
21. Blankensteijn J D, de Jong S E, Prinssen M, van der Ham A C, Buth J, van Sterkenburg S M, et al. Two-year outcomes after conventional or endovascular repair of abdominal aortic aneurysms. N Engl J Med 2005 June 9; 352(23):2398-2405.
22. Fransen G A, Vallabhaneni S R, Sr., van Marrewijk C J, Laheij R J, Harris P L, Buth J. Rupture of infra-renal aortic aneurysm after endovascular repair: a series from EUROSTAR registry. Eur J Vasc Endovasc Surg 2003 November; 26(5):487-493.
23. Harris P L, Vallabhaneni S R, Desgranges P, Becquemin J P, van Marrewijk C, Laheij R J. Incidence and risk factors of late rupture, conversion, and death after endovascular repair of infrarenal aortic aneurysms: the EUROSTAR experience. European Collaborators on Stent/graft techniques for aortic aneurysm repair. J Vasc Surg 2000 October; 32(4):739-749.
24. Tiesenhausen K, Hessinger M, Konstantiniuk P, Tomka M, Baumann A, Thalhammer M, et al. Surgical conversion of abdominal aortic stent-grafts—outcome and technical considerations. Eur J Vasc Endovasc Surg 2006 January; 31(1):36-41.
25. Torsello G, Osada N, Florek H J, Horsch S, Kortmann H, Luska G, et al. Longterm outcome after Talent endograft implantation for aneurysms of the abdominal aorta: a multicenter retrospective study. J Vasc Surg 2006 February; 43(2):277-284; discussion 284.
26. van Marrewijk C, Buth J, Harris P L, Norgren L, Nevelsteen A, Wyatt M G. Significance of endoleaks after endovascular repair of abdominal aortic aneurysms: The EUROSTAR experience. J Vasc Surg 2002 March; 35(3):461-473.
27. Rhee J Y, Trocciola S M, Dayal R, Lin S, Chaer R, Kumar N, et al. Treatment of type II endoleaks with a novel polyurethane thrombogenic foam: induction of endoleak thrombosis and elimination of intra-aneurysmal pressure in the canine model. J Vasc Surg 2005; 42:321-328.
28. Uflacker R, Brothers T. Filling of the aneurysmal sac with deac-glucosamine in an animal model of abdominal aortic aneurysm following stent-graft repair. J Cardiovasc Surg 2006; 47:425-436.
29. Melton L I, Bickerstaff L, Hollier L. Changing incidence of abdominal aortic aneurysms: a population-based study. Am J Epidemiol 1984; 120:379-386.
30. Newman A B, et al. Cardiovascular disease and mortality in older adults with small abdominal aortic aneurysms detected by ultrasonography: the cardiovascular health study. Ann Intern Med 2001; 134(3):182-190.
31. Prinssen M, Verhoeven E L, Buth J, Cuypers P W, van Sambeek M R, Balm R, et al. A randomized trial comparing conventional and endovascular repair of abdominal aortic aneurysms. N Engl J Med 2004; 351:1607-1618.
32. Greenhalgh R M, Brown L C, Kwong G P, Powell J T, Thompson S G. Comparison of endovascular aneurysm repair with open repair in patients with abdominal aortic aneurysm (evar trial 1), 30-day operative mortality results: randomised controlled trial. Lancet 2004; 364:843-848.
33. Greenhalgh R M, Brown L C, Powell J T, Thompson S G. Current interpretation of the U K EVAR Trials. Acta Chir Belg 2006 March-April; 106(2):137-138.

TABLE 1

Order of preparation to obtain a chitosan hydrogel with sclerosing properties at physiological pH.

| Order of preparation | Hydrogel formation | Remarks |
| --- | --- | --- |
| CH + STS | N | Precipitation and phase separation of chitosan solution. |
| [CH + STS] + βGP | N | Precipitation and phase separation of chitosan solution. The βGP addition didn't improve the hydrogel formation. |
| [CH + βGP] + STS | N | Phase separation of chitosan solution. |
| CH + βGP | Y | Homogenous and injectable hydrogel without sclerosing properties. |
| CH + [βGP + STS] | Y | Homogenous and injectable hydrogel with sclerosing properties. |

TABLE 2

Influence of STS concentration on rheological characteristics of chitosan hydrogel at 37° C. (2% w/v CH, 20% v/v IOP, 12% w/v βGP).

| Formulation | STS (% w/v) | pH at 23° C. | $t_{gel}$ (min) | $G'_0$ (Pa)* | $G'_\infty$ (Pa)+ |
|---|---|---|---|---|---|
| CH/βGP-STS-0 | 0 | 7.24 | 897 ± 121 | 10 ± 1 | 1213 ± 79 |
| CH/βGP-STS-1 | 1 | 7.30 | Immediate | 40 ± 23 | 1716 ± 402 |
| CH/βGP-STS-2 | 2 | 7.34 | Immediate | 444 ± 21 | 2724 ± 275 |
| CH/βGP-STS-3 | 3 | 7.39 | Immediate | 1357 ± 387 | 3297 ± 351 |

*Initial storage modulus at time 0.
+Storage modulus after one week of gelation.

What is claimed is:

1. A kit for synthesizing a sclerosing embolizing hydrogel, said kit comprising: a first container containing chitosan in an acid solution; and a second container containing β-glycerophosphate disodium salt and sodium tetradecyl sulphate.

2. The kit of claim 1, wherein the first container also contains an imaging contrast agent.

3. The kit of claim 1, further comprising a mixer.

4. The kit of claim 1, wherein the second container contains an aqueous solution in which the β-glycerophosphate disodium salt and the sodium tetradecyl sulphate are dissolved.

5. The kit of claim 2, wherein said imaging contrast agent is selected from the group consisting of: Hypaque Meglumine, Reno, Conray, Renograffin, Hypaque Sodium, Hexabrix, Oxilan, iohexol, iopamidol, iopromide, ioversol, iodixanol, iothalamate and ioxaglate.

6. The kit of claim 5, wherein the imaging contrast agent is iopamidol.

7. The kit of claim 5, wherein the imaging contrast agent is a radiopaque substance.

8. The kit of claim 1, wherein the acid is selected from the group consisting of: acetic acid, ascorbic acid, salicylic acid, phosphoric acid, hydrochloric acid, propionic acid, formic acid, lactic acid and mixtures thereof.

9. The kit of claim 8, wherein the acid is hydrochloric acid.

* * * * *